US010434283B2

(12) United States Patent
Kelly

(10) Patent No.: US 10,434,283 B2
(45) Date of Patent: Oct. 8, 2019

(54) INTERVENTIONAL MEDICAL SYSTEMS, ASSOCIATED ASSEMBLIES AND METHODS

(71) Applicant: Medtronic, Inc., Minneapolis, MN (US)

(72) Inventor: Tomas K Kelly, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 709 days.

(21) Appl. No.: 14/926,827

(22) Filed: Oct. 29, 2015

(65) Prior Publication Data

US 2017/0119999 A1     May 4, 2017

(51) Int. Cl.
| | |
|---|---|
| *A61M 25/00* | (2006.01) |
| *A61N 1/05* | (2006.01) |
| *A61N 1/375* | (2006.01) |
| *A61N 1/372* | (2006.01) |
| *A61M 25/01* | (2006.01) |

(52) U.S. Cl.
CPC .... *A61M 25/0082* (2013.01); *A61M 25/0074* (2013.01); *A61M 25/0147* (2013.01); *A61N 1/0587* (2013.01); *A61N 1/372* (2013.01); *A61N 1/3756* (2013.01); *A61N 1/37205* (2013.01)

(58) Field of Classification Search
CPC .......... A61M 25/0082; A61M 25/0074; A61M 25/0147; A61N 1/0587; A61N 1/372; A61N 1/37205; A61N 1/3756
See application file for complete search history.

(56) References Cited

U.S. PATENT DOCUMENTS

| | | | |
|---|---|---|---|
| 5,109,867 A | * 5/1992 | Twyford, Jr. | ..... A61M 25/0905 403/223 |
| 5,234,437 A | 8/1993 | Sepetka | |
| 5,250,071 A | 10/1993 | Palermo | |
| 5,261,916 A | 11/1993 | Engelson | |
| 5,350,397 A | 9/1994 | Palermo et al. | |
| 5,895,391 A | 4/1999 | Farnholtz | |
| 6,277,125 B1 | 8/2001 | Barry et al. | |
| 6,355,060 B1 | 3/2002 | Lenker et al. | |

(Continued)

OTHER PUBLICATIONS (PCT/US2016/049569) PCT Notification of Transmittal of the International Search Report and the Written Opinion of the International Searching Authority, dated Nov. 8, 2016, 13 pages.

*Primary Examiner* — Jing Rui Ou

(57) ABSTRACT

In an interventional medical system, a tethering member of a catheter assembly and a holding member of a relatively compact implantable medical device are configured to interlock with one another. The tethering member includes an elongate shaft portion and a connector portion coupled to a distal end of the shaft portion, wherein the connector portion is configured to pass through a proximal-facing opening of a cavity defined by the device holding member, and to interlock with the holding member within the cavity. The connector portion of the tethering member includes a lumen extending longitudinally therethrough, which has a distal opening in fluid communication with the cavity of the device holding member, when the connector portion interlocks therewith. The catheter assembly further includes an elongate mandrel, which has a distal tip configured to extend within the lumen of the tethering member connector portion, being in sliding engagement therewith.

8 Claims, 9 Drawing Sheets

(56) References Cited

U.S. PATENT DOCUMENTS

| | | |
|---|---|---|
| 6,409,674 B1 | 6/2002 | Brockway et al. |
| 6,501,993 B2 | 12/2002 | Morgan et al. |
| 6,554,794 B1* | 4/2003 | Mueller ............ A61B 17/3478 |
| | | 604/528 |
| 6,953,473 B2 | 10/2005 | Porter |
| 7,344,553 B2 | 3/2008 | Opolski et al. |
| 7,371,215 B2* | 5/2008 | Colliou .............. A61N 1/36007 |
| | | 600/104 |
| 7,473,266 B2 | 1/2009 | Glaser |
| 7,647,109 B2* | 1/2010 | Hastings ............. A61N 1/0587 |
| | | 607/32 |
| 7,650,186 B2 | 1/2010 | Hastings et al. |
| 8,364,280 B2 | 1/2013 | Marnfeldt et al. |
| 8,504,156 B2 | 8/2013 | Bonner et al. |
| 8,527,068 B2 | 9/2013 | Ostroff |
| 8,777,932 B2 | 7/2014 | Sage et al. |
| 2002/0077556 A1* | 6/2002 | Schwartz ............ A61B 5/0031 |
| | | 600/486 |
| 2002/0165461 A1* | 11/2002 | Hayzelden ......... A61B 18/1492 |
| | | 600/523 |
| 2003/0097128 A1* | 5/2003 | Hayzelden ......... A61B 18/1492 |
| | | 606/41 |
| 2005/0107667 A1* | 5/2005 | Danitz ................. A61B 1/0053 |
| | | 600/139 |
| 2006/0287700 A1 | 12/2006 | White et al. |
| 2007/0135883 A1* | 6/2007 | Drasler ................ A61B 5/6848 |
| | | 607/126 |
| 2007/0239248 A1* | 10/2007 | Hastings ............. A61N 1/0587 |
| | | 607/127 |
| 2008/0109054 A1* | 5/2008 | Hastings ............. A61N 1/0573 |
| | | 607/127 |
| 2009/0204170 A1 | 8/2009 | Hastings et al. |
| 2010/0331776 A1* | 12/2010 | Salahieh ........... A61M 25/0136 |
| | | 604/95.04 |
| 2012/0165827 A1 | 6/2012 | Khairkhahan et al. |
| 2013/0116704 A1 | 5/2013 | Geistert |
| 2014/0039591 A1* | 2/2014 | Drasler ................ A61B 5/6848 |
| | | 607/126 |
| 2014/0163579 A1 | 6/2014 | Tischendorf et al. |
| 2015/0051609 A1 | 2/2015 | Schmidt et al. |
| 2015/0051611 A1 | 2/2015 | Schmidt et al. |
| 2015/0051682 A1 | 2/2015 | Schmidt et al. |
| 2015/0273207 A1 | 10/2015 | Tran et al. |

* cited by examiner

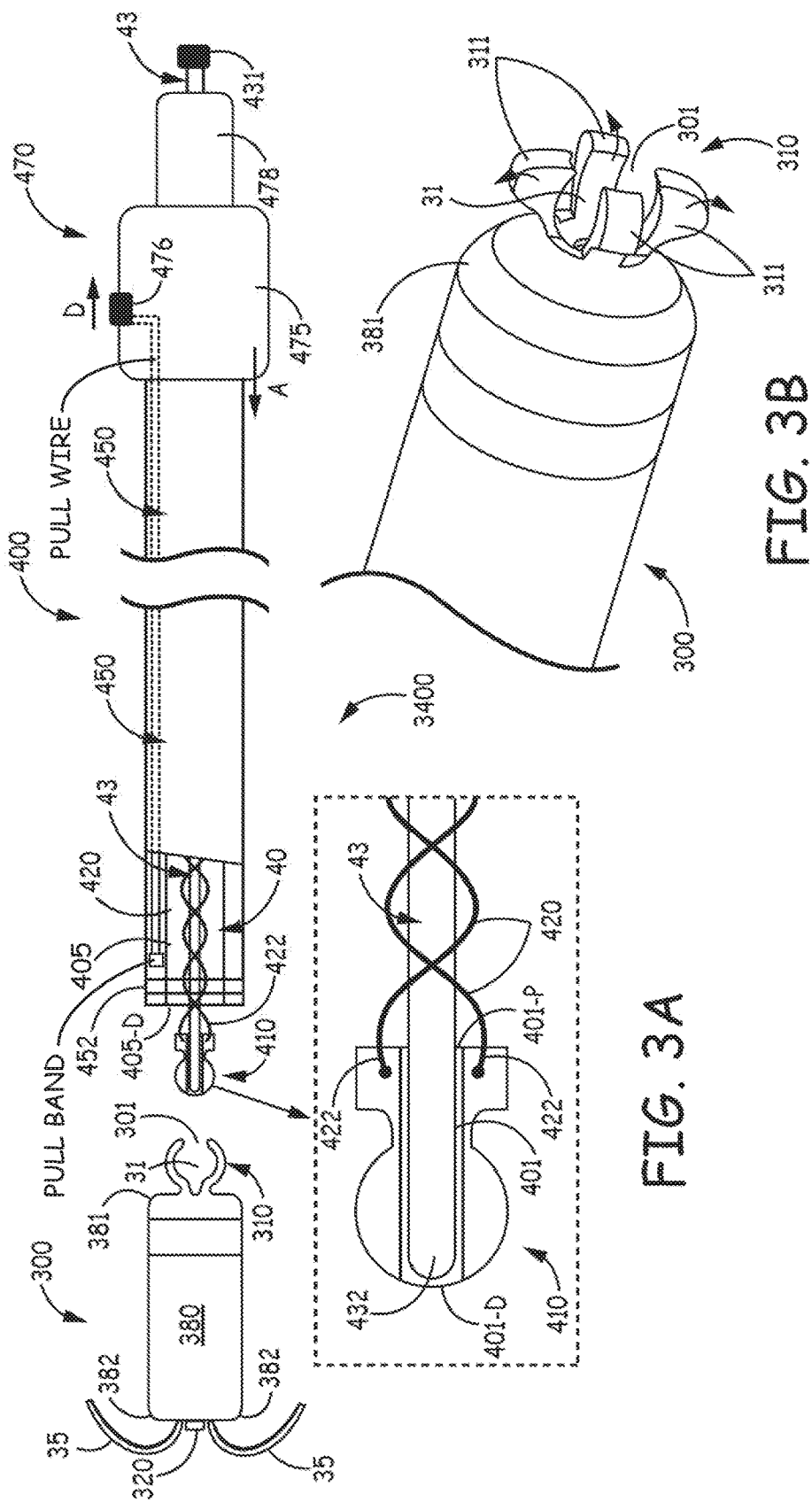

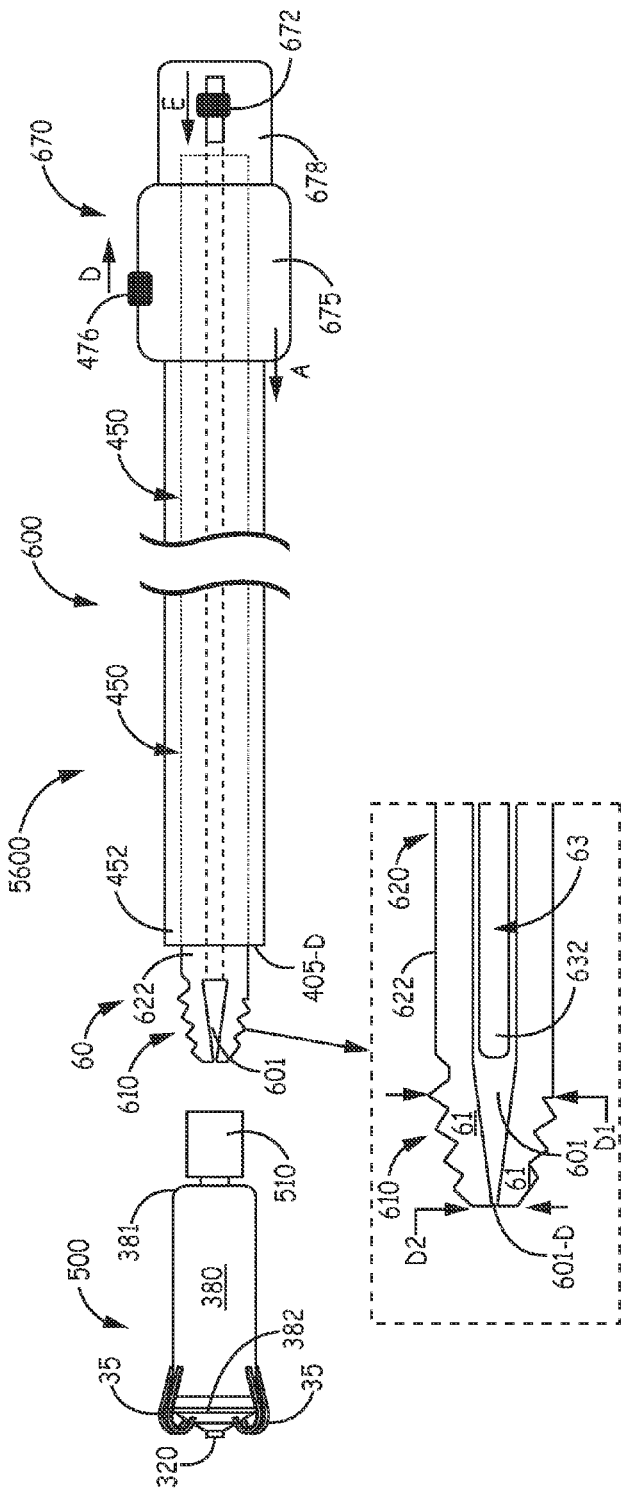
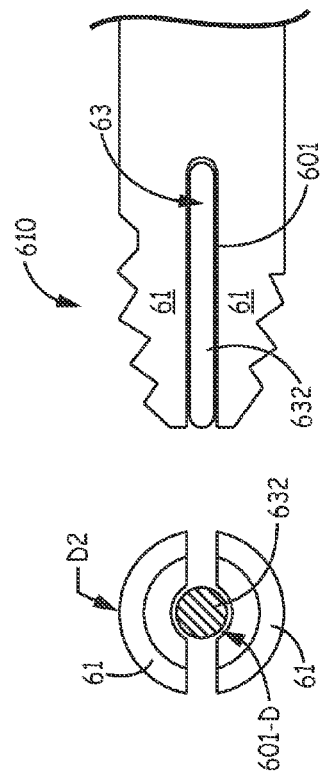
FIG. 6A
FIG. 6B

INTERVENTIONAL MEDICAL SYSTEMS, ASSOCIATED ASSEMBLIES AND METHODS

FIELD OF THE DISCLOSURE

The present disclosure pertains to interventional medical systems, and more particularly to those that include relatively compact medical devices and catheter assemblies that are useful for delivering the devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV, for example, as shown in FIG. 2.

FIG. 2 illustrates an exemplary relatively compact implantable medical device 100 having been delivered through a catheter 200, which an operator has maneuvered up through the inferior vena cava IVC and the right atrium RA into the right ventricle RV. Device 100 and catheter 200 may be similar to the device and tool, respectively, described in the commonly assigned United States Patent Application US 2015/0094668. Device 100 is shown fixed at an implant site by a fixation member 115 thereof, but still secured to catheter 200 by a flexible tether 280 that extends out from distal opening 203 of catheter 200, being joined to a holding member 121 of device 100. Thus, the operator, via tether 280, is able to test the fixation of device 100 at the implant site, and/or remove device 100 from the implant site for repositioning at a more suitable site, if necessary. Once satisfied with the implant of device 100, the operator can separate tether 280 from device 100, for example, by releasing an end of one length 281 of tether 280, and then pulling on an end of another length 282 of tether 280 to withdraw an entirety of length 282 proximally through delivery catheter 200 so that tether length 281 is pulled distally and through device holding member 121.

Securing device 100 to catheter 200 with tether 280 is typically accomplished by a process in which tether 280 is looped through device holding member 121, after which first and second lengths 281, 282 of tether 280 are threaded through one or more lumens of catheter 200 such that opposing ends thereof protrude out from a proximal opening 201 of catheter 200. Because this process may be somewhat tedious a manufacturer of device 100 and catheter 200 may secure the two together as a system, and provide the system to the operator in a single sterile package. However, due to shelf life considerations, the packaging of such a device separately from the associated catheter may be preferred, so that alternative means for securing the device to the catheter may be necessary to increase the ease by which an operator may load the device into the catheter at the time of an implant procedure.

SUMMARY

Embodiments of interventional medical systems, disclosed herein, include a relatively compact implantable medical device and a catheter, wherein a tethering member of an assembly of the catheter and a holding member of the medical device are configured to interlock with one another. The assembly may be an inner assembly of the catheter that extends within a lumen of an outer tubular member of the catheter, being in sliding engagement therewith, and a distal-most opening of the outer tubular member lumen allows passage of the medical device therethrough.

According to some embodiments, the tethering member of the catheter assembly includes an elongate shaft portion and a connector portion coupled to a distal end of the shaft portion, wherein the connector portion is configured to pass through a proximal-facing opening of a cavity defined by the device holding member, and to interlock with the holding member within the cavity. The connector portion of the tethering member includes a lumen extending longitudinally therethrough, which has a distal opening in fluid communication with the cavity of the device holding member, when the connector portion interlocks therewith. The catheter assembly further includes an elongate mandrel, which has a distal tip configured to extend within the lumen of the tethering member connector portion, being in sliding engagement therewith.

In some embodiments, a spherical element forms the connector portion of the catheter assembly tethering member, and the device holding member may include a plurality of elastically deformable arms spaced apart from one another around a perimeter of the cavity, wherein free ends of the arms define the proximal-facing opening of the cavity, through which the spherical element may be passed to interlock with the holding member. According to some methods, an operator can separate the tethering member of the catheter from the interlocked medical device holding member, for example, after advancing the catheter within a patient's vascular system and engaging a fixation member of the device with tissue at an implant site, by sliding the mandrel of the catheter assembly distally relative to the tethering member and through the distal opening of the connector portion lumen, to engage the distal tip with the proximal end of the device housing while applying a pull force through the shaft portion of the tethering member.

According to some alternate embodiments, opposing elastically deformable jaw elements form the connector portion of the catheter assembly tethering member. The jaw elements, which may include toothed outer surfaces, are biased toward one another such that the outer surfaces thereof taper from a first diameter at fixed ends of the jaw elements to a smaller, second diameter at free ends of the jaw elements, and such that the lumen of the connector portion tapers from a first diameter at the fixed ends to a smaller, second diameter at the distal opening of the lumen of the connector portion, wherein the smaller, second diameters of the connector portion outer surfaces and lumen are expandable by insertion of the distal tip of the mandrel, through the lumen, between the jaw elements. Thus, according to some methods, for example, to load the medical device into the catheter, an operator inserts the connector portion, with the jaw elements biased toward one another, through the proximal-facing opening of the cavity defined by the device holding member, and then slides the mandrel of the catheter assembly distally with respect to the tethering member until the distal tip of the mandrel extends within the lumen of the connector portion and between the jaw elements to expand the outer surface second diameter so that the outer surface interlocks with the device holding member within the cavity thereof.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 3A is a plan view of an interventional medical system, with a partial cross-section view, and including an enlarged cross-section view of a portion thereof, according to some embodiments of the present invention;

FIG. 3B is a perspective view of a portion of an exemplary implantable medical device, according to some embodiments;

FIG. 6A is a plan view of an interventional medical system, including an enlarged cross-section view of a portion thereof, according to some alternate embodiments of the present invention;

FIG. 6B is a plan view and corresponding end view of a portion of an inner assembly of a catheter of the system of FIG. 6A, according to some embodiments.

DETAILED DESCRIPTION

Figure 1:
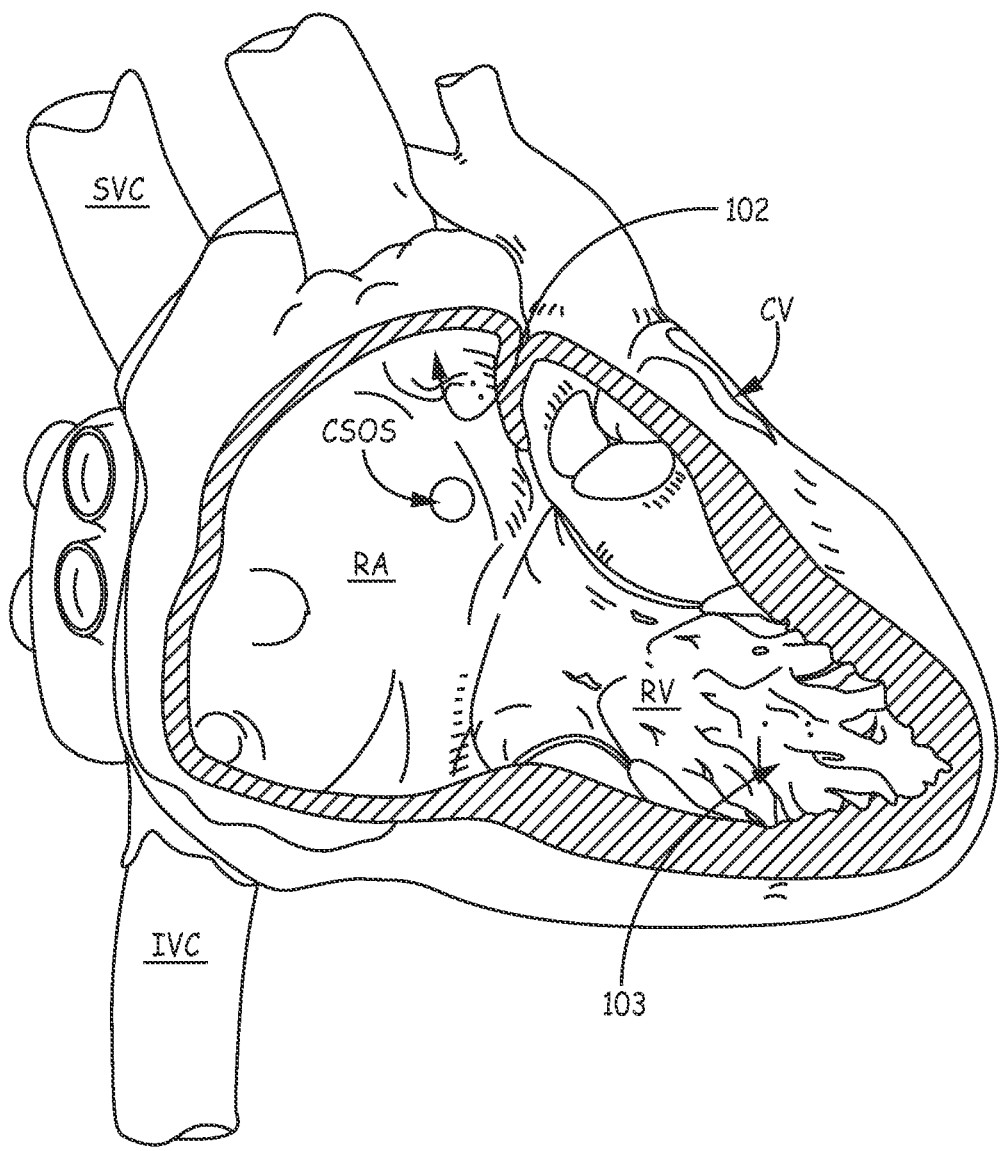
FIG. 1 is a schematic diagram showing potential implant sites for a relatively compact implantable medical device.
Figure 2:
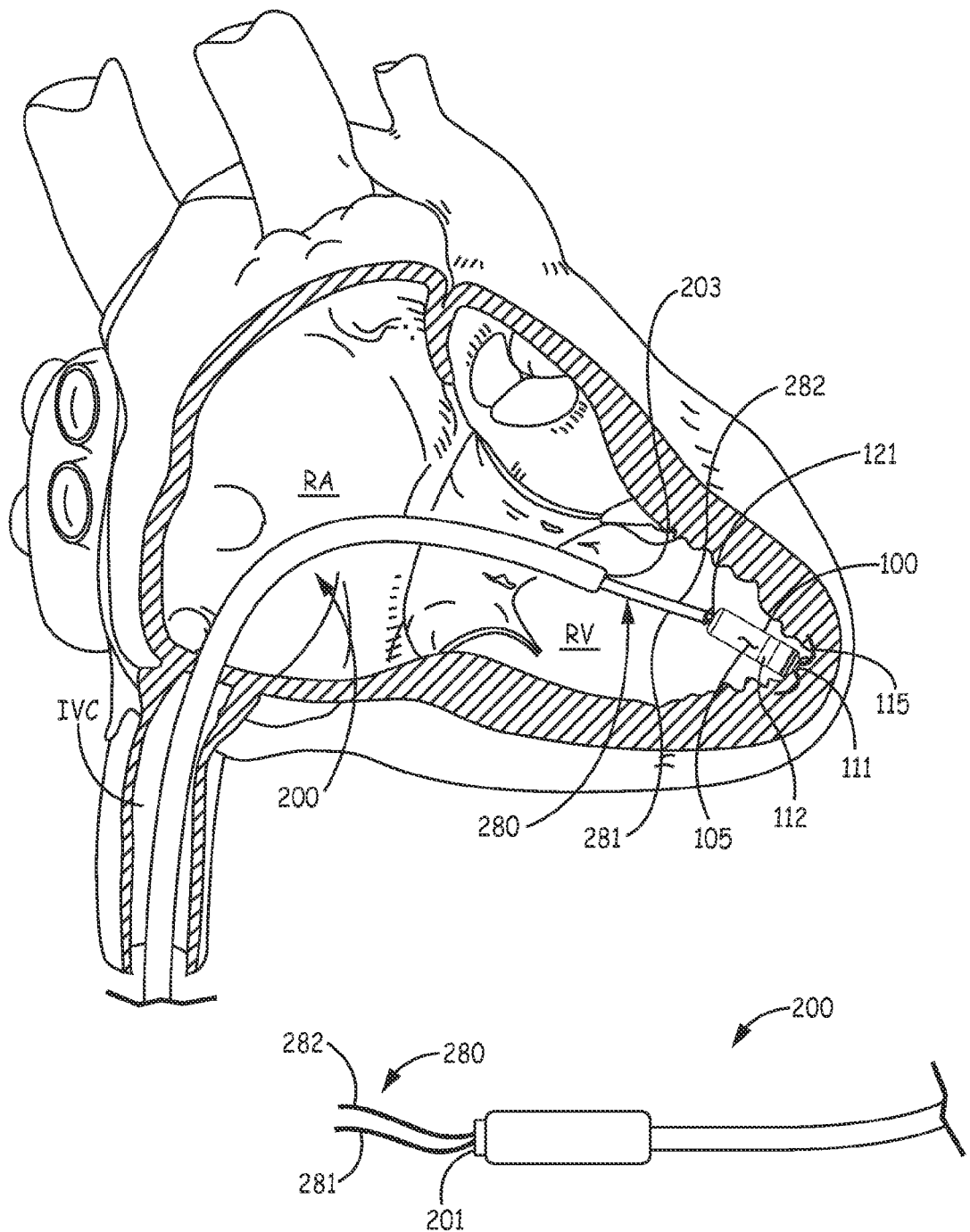
FIG. 2 is a schematic showing an exemplary relatively compact implantable medical device having been delivered from a catheter to an implant site.

The following detailed description is exemplary in nature and is not intended to limit the scope, applicability, or configuration of the invention in any way. Rather, the following description provides practical examples, and those skilled in the art will recognize that some of the examples may have suitable alternatives.

FIG. 3A is a plan view of an interventional medical system 3400, with a partial cross-section view through a catheter 400 thereof, and including an enlarged cross-section view of a portion of an inner assembly of catheter 400, according to some embodiments of the present invention. FIG. 3A illustrates and outer tubular member 450 of catheter 400 including an elongate lumen 405, in which the inner assembly of catheter 400 extends, being in sliding engagement therewith. The inner assembly is shown including a tethering member 40 and an elongate mandrel 43 that extends along a length of tethering member 40 and has a proximal end 431 protruding from a proximal opening of a handle 470 of catheter 400. FIG. 3A further illustrates tethering member 40 including an elongate shaft portion 420 and a connector portion 410 coupled to a distal end 422 of shaft portion 420. According to the illustrated embodiment, a proximal end of shaft portion 420 is coupled to a proximal portion 478 of catheter handle 470, and a proximal end of outer tubular member 450 is coupled to a distal portion 475 of handle 470 which is movable relative to handle proximal portion 478, to advance and retract outer tubular member 450 relative to the inner assembly. FIG. 3A shows outer tubular member 450 retracted so that connector portion 410 of inner assembly tethering member 40 is exposed distal to a distal-most opening 405-D of outer tubular member lumen 405. Distal-most opening 405-D allows passage of a relatively compact implantable medical device therethrough, for example, a medical device 300 of system 3400, which is shown positioned in proximity to tethering member connector portion 410, being oriented for interlocking therewith, as described in further detail below.

With further reference to FIG. 3A, connector portion 410 of tethering member 40 is showing having a lumen 401 extending longitudinally therethrough from a proximal opening 401-P thereof to a distal opening 401-D thereof, wherein a distal tip 432 of mandrel 43 is configured to extend within lumen 401, being in sliding engagement therewith. Connector portion 410 is configured, for example, being formed by a spherical element, to pass through a proximal opening 301 of a cavity 31, which is formed by a holding member 310 of device 300, and to interlock with holding member 310 within cavity 31. According to an exemplary embodiment, connector portion 410 may be machined from a medical grade metal (e.g., stainless steel or titanium).

With reference to the perspective view of FIG. 3B, according to some embodiments, device holding member 310 is formed by a plurality of elastically deformable arms 311 spaced apart from one another around a perimeter of cavity 31, wherein a fixed end of each arm 311 is attached to a proximal end 381 of a hermetically sealed housing 380 of medical device 300 and a free end of each arm 311 defines proximal-facing opening 301 of cavity 31. Arms 311 may be formed from medical grade titanium or stainless steel. An arrow associated with each arm 311 in FIG. 3B indicates the elastic deformation thereof when connector portion 410 of catheter inner assembly tethering member 40 is inserted through proximal-facing opening 301 toward cavity 31. FIG. 3A shows medical device 300 oriented with proximal facing opening 301 of holding member cavity 31 directed toward connector portion 210 of tethering member 40, for insertion of connector portion 210 therethrough to interlock with holding member 310, for example, as illustrated in FIG. 4A.

Figure 3C:
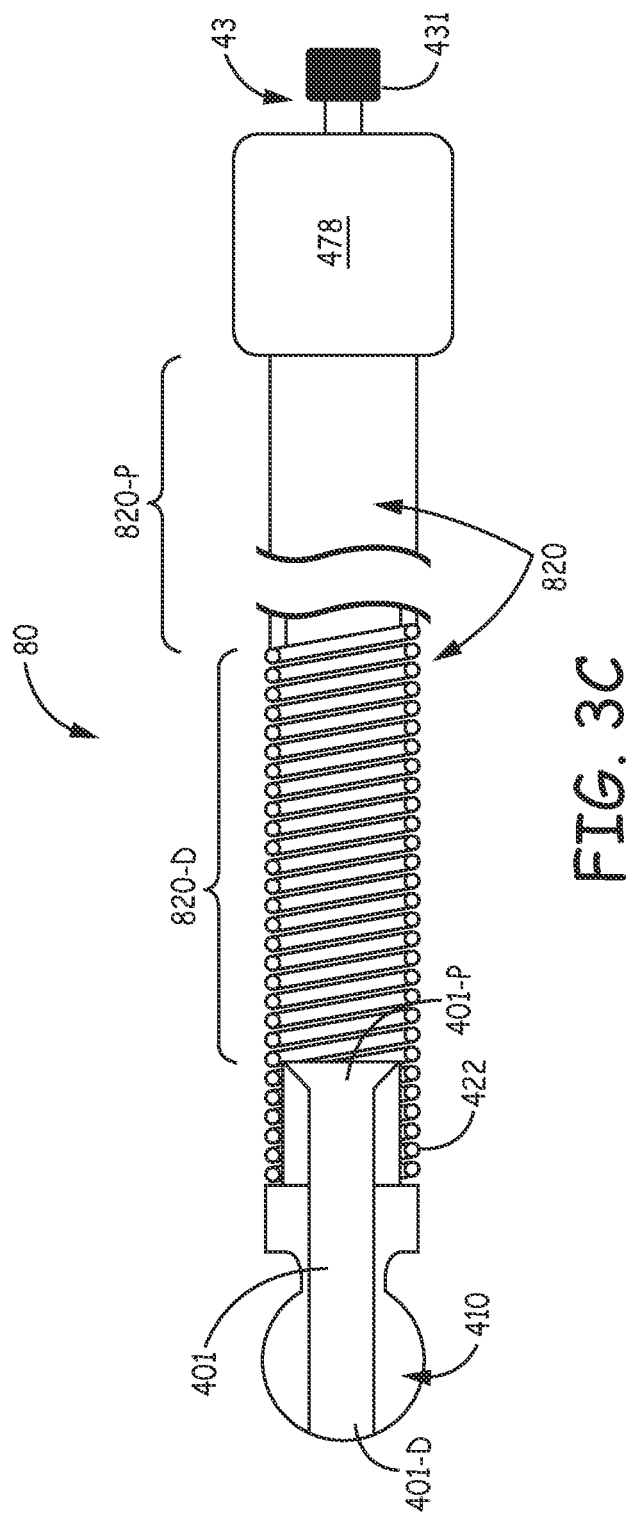
FIG. 3C is a plan view, with a partial longitudinal cross-section, of a tethering member of a catheter, according to some embodiments.
Figure 4A:
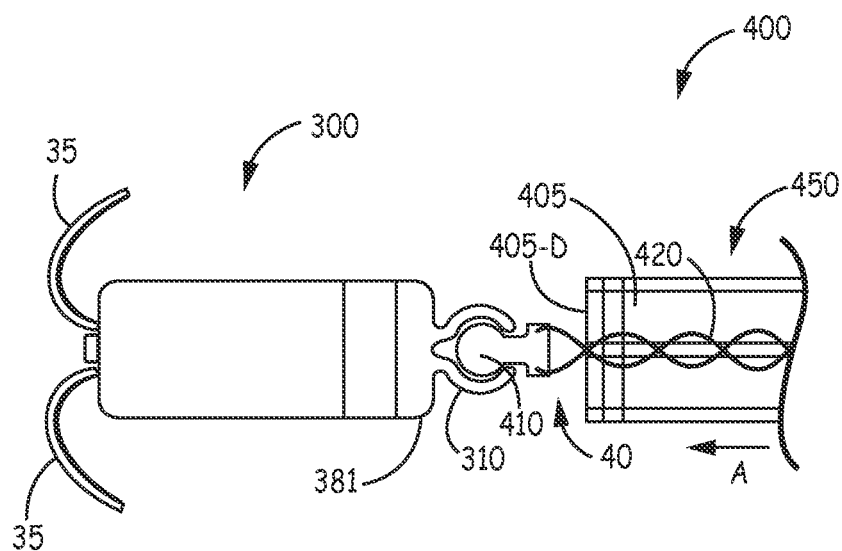
FIGS. 4A-D and 5 are schematics showing portions of the system of FIG. 3A, according to some embodiments, to outline some methods of the present invention.

FIG. 3A further illustrates shaft portion 420 of catheter inner assembly tethering member 40 being formed, at least in part, by a pair of highly flexible cables, so that sliding mandrel distal tip 432 into connector portion lumen 401 allows mandrel 43 to provide some back-up stiffness when inserting connector portion 410 into cavity 31. Further detail concerning the flexibility of shaft portion 420, and a significance thereof, is presented below, in conjunction with FIGS. 3C and 5. According to an exemplary embodiment, mandrel 43 is from a medical grade stainless steel rod, for example, having a diameter of approximately 0.020 inch (0.5 mm).

Figure 4B:
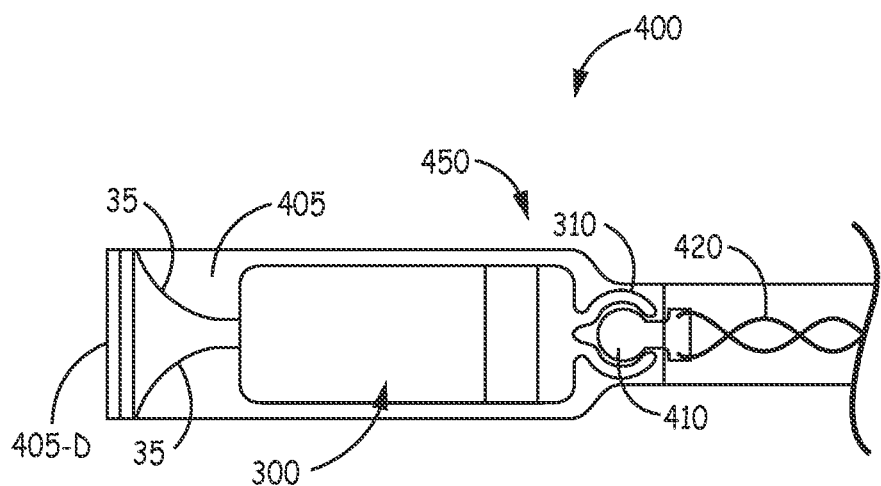

Hermetically sealed housing 380 of device 300 may contain an electronic controller (not shown), for example, a pulse generator and an associated power supply, wherein an electrode 320 of device, which is shown mounted to a distal end 382 of housing 380, is electrically coupled to the controller via a hermetically sealed feedthrough assembly (not shown) such as is known in the art. Device 300 may further include a fixation member, for example, formed by a plurality of super-elastic fingers 35 spaced apart from one another around a perimeter of housing distal end 382. Although only two fixation fingers 35 are shown in FIG. 3A, device 300 may include as many as eight. According to an exemplary embodiment, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art. Fixation fingers 35 may be mounted to distal end 382 of device housing 380, for example, in a manner similar to that described for a fixation component 102 in a commonly assigned United States Patent Application 2012/0172690, which description is hereby incorporated by reference. The super-elastic nature of Nitinol allows fingers 35 to elastically deform between a relaxed condition, which is shown, and an extended condition, in which a free end of each finger extends distally away from distal end 382 of device housing 380, for example, when device 300 is loaded into catheter 400, as shown in FIG. 4B.

According to the illustrated embodiment, fixation fingers 35 are configured to pierce into tissue at the implant site and thereby secure electrode 320 in intimate tissue contact. In some embodiments, device 300 preferably includes a steroid-eluting member (not shown), for example, mounted in, or around electrode 320, which is useful for reducing inflammation of the pierced tissue to maintain effective and efficient pacing via electrode 320. Device housing 380, for example, formed from a biocompatible and biostable metal such as titanium, may be overlaid with an insulative layer, for example, medical grade polyurethane, parylene, or silicone, and device 300 may include another electrode, for example, formed by removing a portion of the insulative layer to expose the metallic surface of housing 380. The other electrode may function in conjunction with electrode 320 for bipolar pacing and sensing.

In some exemplary embodiments, outer tubular member 450 of catheter 400, for example, extending over a length of approximately 100 cm, may be formed by a stainless steel braid-reinforced medical grade polymer, for example, one or more appropriate grades of polyether block amide, which are arranged for decreasing stiffness from handle 470 to a distal end 452 of tubular member 450 (e.g., including PEBAX® 3533, 6333, 4033, and 7233), and lumen 405 of tubular member 450 may have a diameter of approximately 0.3 inch (7.6 mm) in proximity to distal-most opening 405-D, to contain medical device 300 therein. Distal end 452 may have a radiopaque filler blended therein, or a radiopaque marker (e.g., Tungsten-filled Vestamid®) bonded thereto, either according to methods known to those skilled in the art. With further reference to FIG. 3A, a control member 476 for an optional steering assembly of catheter 400 is shown being mounted to handle distal portion 475. The steering assembly, according to configurations known in the art, may further include a pull band mounted in tubular member distal end 452 and an elongate pull wire that extends along a length of tubular member 450, being coupled at a distal end thereof to the pull band and, at a proximal end thereof, to control member 476, such that moving control member 476, per arrow D, causes the pull wire to deflect outer tubular member 450, along with the inner assembly of catheter 400, which deflection may be useful in navigating catheter 400 into proximity with an implant site. Handle 470 may be constructed from injection molded, relatively hard, medical grade plastic parts, according to methods known in the art.

As alluded to above, shaft portion 420 of catheter inner assembly tethering member 40 may include a highly flexible segment distal segment. This flexibility permits an operator to keep control over device 300, by maintaining tethering member connector portion 410 interlocked with device holding member 310, while evaluating a performance of device 300 immediately following the implant thereof, because a stiffness of the distal segment of tethering shaft portion 420 is not significant enough to influence contact between device electrode 320 and tissue at the implant site. Methods related to implanting device 300 with catheter 400 are described in greater detail below, in conjunction with FIGS. 4A-D and 5. FIG. 3A illustrates the distal segment of tethering member shaft portion 420 being formed by the aforementioned pair of highly flexible cables (e.g., 7×7 cables formed from 0.0025" diameter 304 Stainless Steel wire strands, or similar), wherein the cables, at distal end 422, are coupled to a shank of connector portion 410, for example, by adhesive or thermal bonding, or by an overmolded polymer coupling. In some alternate embodiments, the distal segment may be formed by a laser cut hypo-tube, or have a nitinol cage tube construction; or the distal segment may be formed by a coiled wire, for example, as shown in FIG. 3C. FIG. 3C is a plan view, with a partial longitudinal cross-section, of a tethering member 80, according to some alternate embodiments, wherein a highly flexible distal segment 820-D of a shaft portion 820 thereof is formed by a coiled wire, or by a braided shaft formed from concentrically arranged coiled wires, wound in alternate helical directions, for example, to minimize compression without sacrificing flexibility. The wires may be a medical grade metal, for example, 304 stainless steel, and distal segment 820-D may further include a relatively low durometer polymer overlay, for example, PEBAX® 3533 formed by a dip coating process, according to some embodiments. Distal segment 820-D of shaft portion 820 (or that of shaft portion 420) may extend over a length from approximately 25 cm to approximately 30 cm between a proximal segment 820-P of shaft portion 820 (or the proximal segment of shaft portion 420) and connector portion 410. Proximal segment 820-P of shaft portion 820 (or that of shaft portion 420) may be formed from a stainless steel braid-reinforced medical grade polymer, for example, one or more appropriate grades of polyether block amide (e.g., including PEBAX® 3533, 6333, 4033, and 7233), and may include a fluoropolymer liner, for example, PTFE.

Figure 4C:
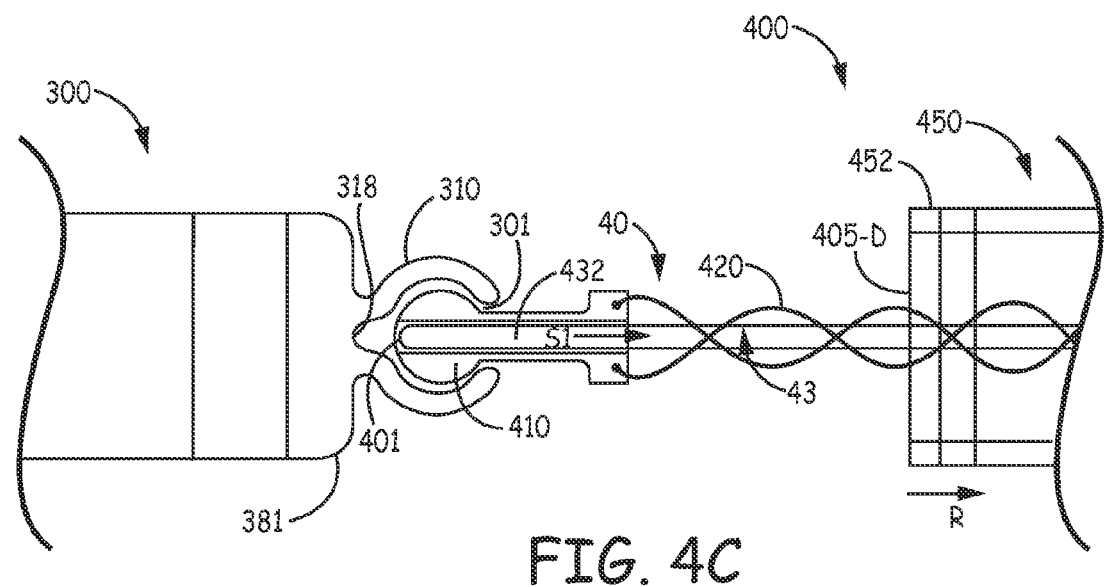
Figure 4D:
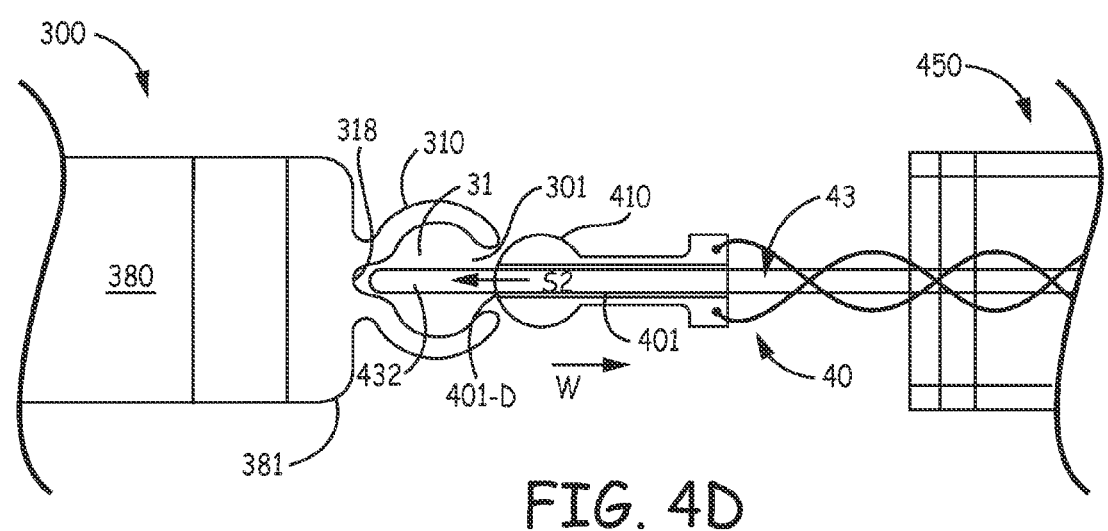
Figure 5:
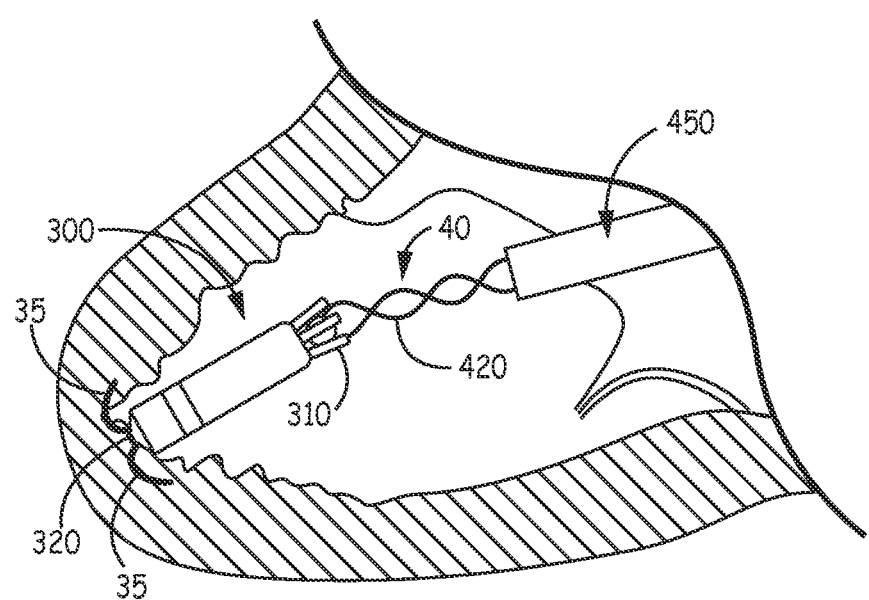

FIGS. 4A-D and 5 are schematics showing portions of the system of FIG. 3A, according to some embodiments, to outline some methods of the present invention. According to some methods, to load a medical device into a catheter, for example, device 300 into catheter 400, an operator may retract outer tubular member 450 of catheter 400 relative to the inner assembly thereof, as described above, so that connector portion 410 of inner assembly tethering member 40 protrudes distally from distal-most opening 405-D of outer tubular member lumen 405, being exposed for interlocking engagement with holding member 310 of device 300. FIG. 4A illustrates connector portion 410 of catheter inner assembly tethering member 40 being interlocked with device holding member 300, as described above in conjunction with FIGS. 3A-B. After interlocking connector portion 410 with device holding member 310, the operator may advance outer tubular member 450, per arrow A, relative to the inner assembly of catheter 400 and device 300, for example, by moving handle distal portion 475 relative to handle proximal portion 478 (FIG. 3A), until tubular member lumen 405 contains connector portion 410 and the interlocked device 300, as shown in FIG. 4B. Once device 300 is loaded in catheter 400, the operator may advance catheter 400 within a patient's vascular system to position device fixation fingers 35 in proximity with an implant site, for example, any of the cardiac implant sites mentioned above in conjunction with FIG. 1, so the operator may engage fixation fingers 35 with tissue at the implant site, for example, by retracting outer tubular member 450 of catheter 400, relative to device 300 and the inner assembly, per arrow R of FIG. 4C. With further reference to FIG. 4C, the operator may have positioned distal tip 432 of inner assembly mandrel 43 within connector portion lumen 401, either before or after advancing catheter 400, to provide some back-up stiffness to tethering member shaft portion 420. When device fixation fingers 35 are engaged with tissue at the implant site, the operator may separate tethering member 40 from device 300, for example as illustrated in FIG. 4D. But, according to some methods, before separating tethering member, the operator may slide mandrel 43 proximally, per arrow S1 of FIG. 4C, to restore the above-described highly flexible property of tethering member shaft portion 420, and then evaluate a performance of device 300 at the implant site, as illustrated in FIG. 5. As was mentioned above, a stiffness of the distal segment of tethering shaft portion 420 is not significant enough to influence contact between device electrode 320 and tissue at the implant site, so the operator may test the function of electrode 320 and then determine if device 300 may remain at the implant site or if device 300 needs to be re-positioned. With reference to FIG. 4D, according to some methods, if the operator is satisfied with the device performance, the operator withdraws tethering member connector portion 410 from cavity 31 defined by device holding member 310, through proximal-facing opening 301 thereof, by sliding mandrel 43 distally, per arrow S2, to engage mandrel distal tip 432 with proximal end 381 of device housing 380 while applying a pull force, per arrow W, through tethering member shaft portion 420. According to some embodiments, device housing proximal end 381 includes a recess 318 formed therein, as seen in FIGS. 4C-D, to receive mandrel distal tip 432 as connector portion 410 is withdrawn from cavity 31.

FIG. 6A is a plan view of an interventional medical system 5600, including an enlarged cross-section view of a portion thereof, according to some alternate embodiments. FIG. 6A illustrates a catheter 600 of system 5600 including outer tubular member 450, like catheter 400 of system 3400 described above, but an inner assembly of catheter 600, which extends along outer tubular member 450, being in sliding engagement within lumen 405 thereof, differs from that of catheter 400. Outer tubular member 450 of catheter 600 is shown retracted relative to the inner assembly such that a connector portion 610 of a tethering member 60 of the inner assembly is exposed distal to distal-most opening 405-D of outer tubular member lumen 405. With reference to the enlarged cross-section view of FIG. 6A, connector portion 610 is coupled to a distal end 622 of an elongate shaft portion 620 of tethering member 60. Dotted lines in the plan view of catheter 600 represent shaft portion 620 extending within lumen 405 of outer tubular member 450 from distal end 622 to a proximal end of shaft portion 620, which is coupled to a proximal portion 678 of a handle 670 of catheter 600. FIG. 6A further illustrates tethering member connector portion 610 being formed by opposing elastically deformable jaw elements 61, wherein each jaw element 61 extends distally from a fixed end thereof to a free end thereof and has a toothed outer surface. According to the illustrated embodiment, jaw elements 61 are biased toward one another such that the outer surfaces thereof taper from a first diameter D1 at the fixed ends of jaw elements 61 to a smaller, second diameter D2 at the free ends of jaw elements 61. In an exemplary embodiment, connector portion 610 is formed from a relatively hard medical grade plastic, such as PEBAX® 7233 or similar, for example, by injection molding; and shaft portion 620 is formed from a stainless steel braid-reinforced medical grade polymer, for example, one or more appropriate grades of polyether block amide, which are arranged for decreasing stiffness from handle proximal portion 678 to shaft portion distal end 622 (e.g., PEBAX® 7233-6333-5533-4033-3533). According to an alternate embodiment, shaft portion 620 may be constructed with a proximal segment and a significantly more flexible distal segment, for example, like shaft portion 820 of inner assembly tethering member 40 of catheter 400 described above.

With further reference to FIG. 6A, the inner assembly of catheter 600 also includes an elongate mandrel 63, which may be very similar to mandrel 43 of catheter 400 described above, and which is shown extending along a length of tethering member shaft portion 620, as indicated by dashed lines in the plan view of catheter 600. According to the illustrated embodiment, a proximal end of mandrel 63 is coupled to a control member 672 that is mounted to handle proximal portion 678. Control member 672 may be moved, per arrow E, to slide mandrel 63 distally with respect to tethering member 60. The enlarged cross-section view of FIG. 6A shows a distal tip 632 of mandrel 63 extending within a lumen 601 of tethering member connector portion 610, which tapers from a first diameter at the fixed ends of jaw elements 61 to a smaller, second diameter at a distal opening 601-D of lumen 601, which is coincident with the free ends of jaw elements 61. According to the illustrated embodiment, the smaller, second diameter of lumen 601 and second diameter D2 of the outer surfaces of connector portion 610 are expandable by sliding mandrel distal tip 632 distally through lumen 601 and between jaw elements 61, as shown in the plan view and corresponding end view of FIG. 6B. When expanded by mandrel 63, as shown, connector portion 610 interlocks with a holding member 510 of a relatively compact medical device 500 of system 5600, as described below. FIG. 6A shows device 500 of system 5600 including features common with device 300, except for holding member 510, and being positioned and oriented for loading into catheter 600.

Figure 7A:
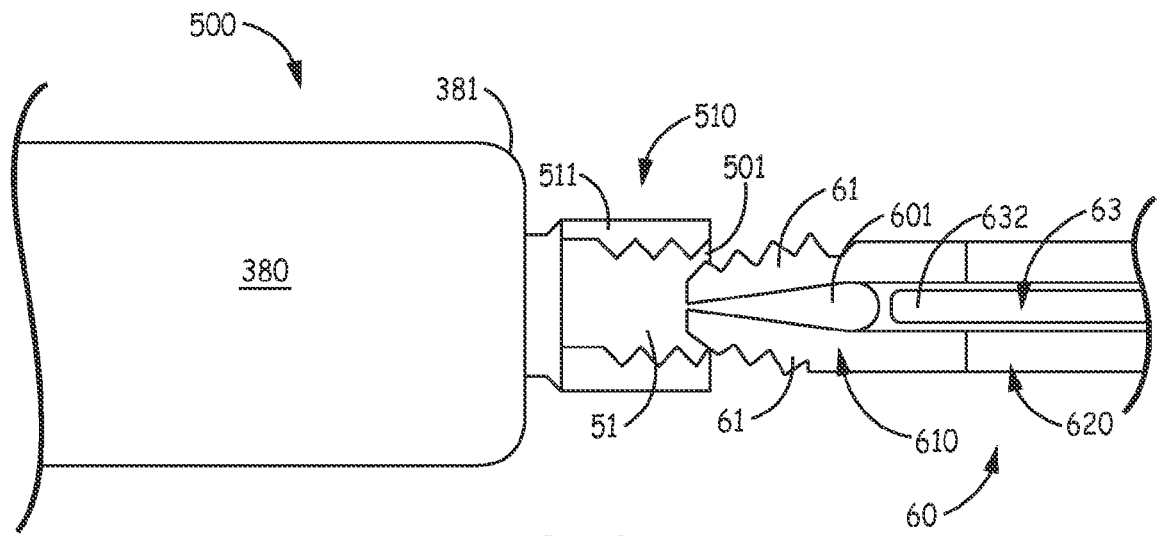
FIGS. 7A-B are schematics outlining some method steps associated with the system of FIGS. 6A-B.
Figure 7B:
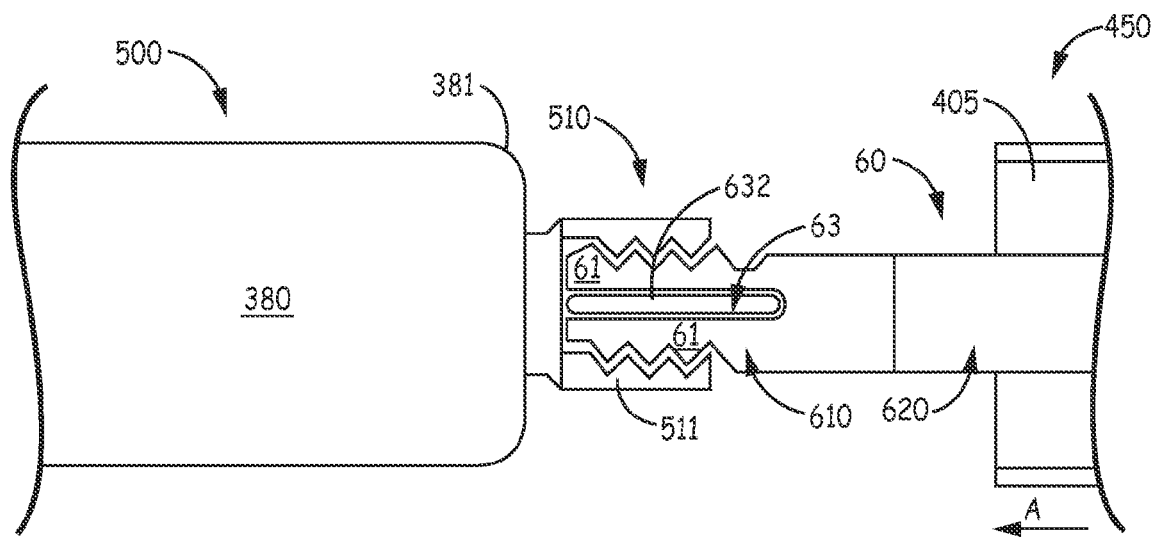

FIGS. 7A-B are schematics outlining some steps of a method for loading medical device 500 into catheter 600. FIGS. 7A-B illustrate holding member 510 of device 500 being formed by a relatively rigid sidewall 511 that has an inner surface defining a cavity 51 of holding member 510, wherein the inner surface has a toothed contour to interlock with the toothed outer surfaces of jaw elements 61 of connector portion 610 of catheter inner assembly tethering member 60. In FIG. 7A, jaw elements 61 are shown biased toward one another, with the outer surfaces thereof tapered, as described above, so that an operator may insert connector portion 610 through a proximal-facing opening 501 of device holding member cavity 51. Once the connector portion 610 is fully inserted within cavity 51, for example, when the free ends of jaw elements 61 bottom out, the operator can slide mandrel distal tip 632 distally through lumen 601 and between jaw elements 61, for example, by moving control member 672 per arrow E (FIG. 6A), to cause the outer surfaces of connector portion 610 to expand and interlock with device holding member 510, within cavity 51, as shown in FIG. 7B. Once device 500 is interlocked with tethering member 60, the operator may advance outer tubular member 450 of catheter 600 relative to the inner assembly of catheter 600 and device 500, for example, by moving a distal portion 675 of catheter handle 670, which is coupled to a proximal end of outer tubular member 450 (FIG. 6A), relative to handle proximal portion 678, per arrow A, until device 500 is contained within lumen 405 of tubular member 450, for example, in a similar fashion to that shown for device 300 in FIG. 4B.

In the foregoing detailed description, the invention has been described with reference to specific embodiments. However, it may be appreciated that various modifications and changes can be made without departing from the scope of the invention as set forth in the appended claims.

For example, the following Items are illustrative of further embodiments:

Item 1. An interventional medical system comprising a relatively compact implantable medical device and a catheter; the medical device comprising a hermetically sealed housing, and a holding member connected to a proximal end of the housing, the holding member defining a cavity that has a proximal-facing opening; the catheter comprising an elongate inner assembly and an elongate outer tubular member, the outer tubular member including an elongate lumen extending along a length thereof and including a distal-most opening formed at a distal end of the outer tubular member, the distal-most opening allowing passage of the medical device therethrough, and the inner assembly extending along, and being in sliding engagement within the lumen of the outer tubular member; and the catheter inner assembly comprising:
 a tethering member including an elongate shaft portion and a connector portion coupled to a distal end of the shaft portion, the connector portion being configured to pass through the proximal-facing opening of the device holding member cavity and to interlock with the holding member within the cavity, and the connector portion having a lumen extending longitudinally therethrough from a proximal opening thereof, in proximity to the distal end of the shaft portion, to a distal opening thereof, the distal opening of the connector portion lumen being in fluid communication with the cavity of the device holding member when the connector portion interlocks therewith; and
 an elongate mandrel extending longitudinally along a length of the tethering member, the mandrel including a proximal end and a distal tip, the proximal end extending proximally from lumen of the outer tubular member, and the distal tip being configured to extend within the lumen of the tethering member connector portion, being in sliding engagement therewith.

Item 2. The system of item 1, wherein the shaft portion of the tethering member of the catheter inner assembly includes a highly flexible distal segment, the distal segment comprising one of: a pair of cables, at least one coiled wire, and a laser cut tubing.

Item 3. The system of any one of items 1-2, wherein:
 the distal tip of the mandrel of the catheter inner assembly is configured to pass through the distal opening of the connector portion of the catheter inner assembly tethering member; and
 the proximal end of the device housing includes a recess formed therein, the recess being in fluid communication with the cavity of the holding member and configured to receive the distal tip of the mandrel of the catheter inner assembly.

Item 4. The system of any one of items 1-3, wherein the holding member of the medical device comprises a plurality of elastically deformable arms spaced apart from one another around a perimeter of the cavity, each arm extending from a fixed end thereof to a free end thereof, the fixed ends being attached to the proximal end of the device housing, and the free ends defining the proximal-facing opening of the cavity.

Item 5. The system of item 4, wherein the connector portion of the tethering member of the catheter inner assembly comprises a spherical element.

Item 6. The system of any one of items 1-5, wherein:
 the connector portion of the tethering member of the catheter inner assembly comprises opposing elastically deformable jaw elements;
 each jaw element extends distally from a fixed end thereof to a free end thereof and has a toothed outer surface; and
 the jaw elements are biased toward one another such that the outer surfaces thereof taper from a first diameter at the fixed ends of the jaw elements to a smaller, second diameter at the free ends of the jaw elements, and such that the lumen of the connector portion tapers from a first diameter at the fixed ends of the jaw elements to a smaller, second diameter at the distal opening of the lumen of the connector portion, the distal opening being coincident with the free ends of the jaw elements, and the smaller, second diameters of the connector portion outer surfaces and lumen being expandable by sliding the mandrel distal tip distally through the connector portion lumen and between the jaw elements.

Item 7. The system of item 6, wherein the holding member of the medical device comprises a relatively rigid sidewall having an inner surface that defines the cavity, the inner surface having a toothed contour to interlock with the toothed outer surfaces of the jaw elements of the connector portion of the catheter inner assembly tethering member.

Item 8. The system of any one of items 1-7, wherein:
 the catheter further comprises a handle coupled to the outer tubular member and the inner assembly thereof; and
 the handle includes a distal portion secured to a proximal end of the outer tubular member, and a proximal portion secured to a proximal end of the shaft portion of the inner assembly tethering member, the handle distal portion being configured to advance and retract the outer tubular member relative to the inner assembly.

Item 9. The system of item 8, wherein the inner assembly of the catheter further comprises a control member coupled to the proximal end of the mandrel and mounted to the proximal portion of the handle, the control member being configured to slide the mandrel longitudinally with respect to the tethering member.

Item 10. The system of item 8, wherein the catheter further comprises a steering assembly, the steering assembly including a pull wire, a pull band, and a control member, the control member being mounted to the distal portion of the handle, the pull band being mounted to the outer tubular member in proximity to the distal end thereof, and the pull wire extending along a length of the outer tubular member from a proximal end of the pull wire to a distal end of the pull wire, the proximal end of the pull wire being coupled to the control member, and the distal end of the pull wire being coupled to the pull band.

Item 11. The system of any one of items 1-11, wherein:

the catheter further comprises a handle coupled to the outer tubular member and the inner assembly thereof; and the inner assembly of the catheter further comprises a control member coupled to the proximal end of the mandrel and mounted to the handle, the control member being configured to slide the mandrel longitudinally with respect to the tethering member.

Item 12. A catheter assembly for delivering an implantable medical device to an implant site within a patient's vascular system, the assembly comprising:

a tethering member including an elongate shaft portion and a connector portion coupled to a distal end of the shaft portion, the connector portion being configured to pass through a proximal-facing opening of a cavity of a holding member of the medical device and to interlock with the device holding member within the cavity, and the connector portion having a lumen extending longitudinally therethrough from a proximal opening thereof, in proximity to the distal end of the shaft portion, to a distal opening thereof, the distal opening of the connector portion lumen being in fluid communication with the cavity of the device holding member when the connector portion interlocks therewith; and an elongate mandrel extending longitudinally along a length of the tethering member, the mandrel including a distal tip configured to extend within the lumen of the tethering member connector portion, being in sliding engagement therewith.

Item 13. The assembly of item 12, wherein the shaft portion of the tethering member of the catheter inner assembly includes a highly flexible distal segment, the distal segment comprising one of: a pair of cables, at least one coiled wire, and a laser cut tubing.

Item 14. The assembly of any one of items 12-13, wherein the connector portion of the tethering member comprises a spherical element.

Item 15. The assembly of any one of items 12-14, wherein:
the connector portion of the tethering member comprises opposing elastically deformable jaw elements;
each jaw element extends distally from a fixed end thereof to a free end thereof and has a toothed outer surface; and
the jaw elements are biased toward one another such that the outer surfaces thereof taper from a first diameter at the fixed ends of the jaw elements to a smaller, second diameter at the free ends of the jaw elements, and such that the lumen of the connector portion tapers from a first diameter at the fixed ends of the jaw elements to a smaller, second diameter at the distal opening of the lumen of the connector portion, the distal opening being coincident with the free ends of the jaw elements, and the smaller, second diameters of the connector portion outer surfaces and lumen being expandable by sliding the mandrel distal tip distally through the connector portion lumen and between the jaw elements.

Item 16. The assembly of any one of items 12-15, further comprising:
a handle portion coupled to a proximal end of the shaft portion of the tethering member; and
a control member coupled to a proximal end of the mandrel and mounted to the handle portion, the control member being configured to slide the mandrel longitudinally with respect to the tethering member.

Item 17. A method for loading a medical device into a catheter, the method comprising:

inserting a connector portion of a tethering member of an inner assembly of the catheter into a cavity defined by a holding member of the medical device, through a proximal facing opening thereof, the holding member being mounted to a proximal end of a housing of the device; and sliding a mandrel of the catheter inner assembly distally with respect to the tethering member until a distal tip of the mandrel extends within a lumen of the tethering member connector portion, after inserting the connector portion; and wherein the distal tip of the mandrel extending within the lumen of the tethering member connector portion causes an outer surface of the connector portion to expand and interlock with the device holding member within the cavity thereof.

Item 18. The method of item 17, further comprising advancing an outer tubular member of the catheter relative to the catheter inner assembly, until a lumen of the tubular member contains the connector portion of the inner assembly tethering member and the interlocked medical device.

Item 19. The method of any one of items 17-18, wherein the connector portion of the catheter inner assembly tethering member comprises opposing elastically deformable jaw elements between which the lumen of the connector portion extends, the outer surface of the connector portion comprising a row of teeth extending along each jaw element.

Item 20. A method for delivering an implantable medical device to an implant site within a patient's vascular system, the method comprising:

positioning a distal tip of an elongate mandrel of an inner assembly of a catheter within a lumen of a connector portion of a tethering member of the inner assembly;

interlocking the connector portion of the inner assembly tethering member with a holding member of the medical device by inserting the connector portion into a cavity defined by the holding member, through a proximal facing opening thereof, the holding member being mounted to a proximal end of a housing of the device;

advancing the catheter and the device within the patient's vascular system to position a fixation member of the device in close proximity to the implant site, after interlocking the connector portion of the inner assembly tethering member, the device fixation member being mounted to a distal end of the device housing;

engaging the positioned device fixation member with tissue at the implant site; and withdrawing the connector portion of the tethering member from the cavity defined by the device holding member, through the proximal-facing opening thereof, after engaging the device fixation member with tissue at the implant site, by sliding the mandrel distally relative to the tethering member and through a distal opening of the connector portion lumen, to engage with the proximal end of the device housing while applying a pull force through a shaft portion of the tethering member, the connector portion of the tethering member being coupled to a distal end of the tethering member shaft portion.

Item 21. The method of item 20, further comprising:
advancing an outer tubular member of the catheter relative to the catheter inner assembly, until a lumen of the tubular member contains the connector portion of the inner assembly tethering member and the interlocked medical device, prior to advancing the catheter and the device within the patient's vascular system; and retracting the outer tubular member relative to the interlocked medical device, to expose the device fixation member, after advancing the catheter and the device within the patient's vascular system, and while engaging the positioned device fixation member with the tissue at the implant site.

Item 22. The method of any one of items 20-21, further comprising:
after engaging the positioned device fixation member with tissue at the implant site, and before withdrawing the connector portion of the tethering member from the cavity defined by the device holding member, sliding the mandrel of the catheter inner assembly proximally relative to the tethering member of the catheter inner assembly, until the distal tip of the mandrel is no longer positioned in the lumen of the connector portion of the tethering member and is offset proximally from the connector portion; and
evaluating a performance of the device, after sliding the mandrel of the catheter inner assembly proximally, and before releasing the device.

I claim:

1. An interventional medical system comprising:
an implantable medical device comprising a hermetically sealed housing, an electrode coupled in proximity to a distal end of the housing, a fixation member coupled to the distal end of the housing, and a holding member coupled to a proximal end of the housing, the holding member defining a cavity that has a proximal-facing opening; and
a catheter comprising an elongate inner assembly and an elongate outer tubular member, the outer tubular member including an elongate lumen extending along a length thereof and including a distal-most opening formed at a distal end of the outer tubular member, the distal-most opening allowing passage of the medical device therethrough, and the inner assembly extending along, and being in sliding engagement within the lumen of the outer tubular member; and the catheter inner assembly comprising:
a tethering member including an elongate shaft portion and a connector portion coupled to a distal end of the shaft portion, the connector portion being configured to pass through the proximal-facing opening of the device holding member cavity and to interlock with the holding member within the cavity, and the connector portion having a lumen extending longitudinally therethrough from a proximal opening to a distal opening that is configured to be in fluid communication with the cavity of the device holding member when the connector portion interlocks therewith; and
an elongate mandrel that is in sliding engagement with the lumen of the outer tubular member and the lumen of the tethering member connector portion,
wherein the connector portion is configured to disengage from the holding member as a result of the elongate mandrel extending distally through the proximal-facing opening from the distal opening of the connector portion while applying a pull force through the elongate shaft portion of the tethering member.

2. The system of claim 1, wherein the shaft portion of the tethering member of the catheter inner assembly includes a highly flexible distal segment, the distal segment comprising one of: a pair of cables, at least one coiled wire, and a laser cut tubing.

3. The system of claim 1, wherein:
a distal tip of the mandrel of the catheter inner assembly is configured to pass through the distal opening of the connector portion of the catheter inner assembly tethering member; and
the proximal end of the device housing includes a recess formed therein, the recess being in fluid communication with the cavity of the holding member and configured to receive the distal tip of the mandrel of the catheter inner assembly.

4. The system of claim 1, wherein the holding member of the medical device comprises a plurality of elastically deformable arms spaced apart from one another around a perimeter of the cavity, each arm extending from a fixed end thereof to a free end thereof, the fixed ends being attached to the proximal end of the device housing, and the free ends defining the proximal-facing opening of the cavity.

5. The system of claim 4, wherein the connector portion of the tethering member of the catheter inner assembly comprises a spherical element.

6. The system of claim 1, wherein:
the catheter further comprises a handle coupled to the outer tubular member and the inner assembly thereof; and
the handle includes a distal portion secured to a proximal end of the outer tubular member, and a proximal portion secured to a proximal end of the shaft portion of the inner assembly tethering member, the handle distal portion being configured to advance and retract the outer tubular member relative to the inner assembly.

7. The system of claim 6, wherein the catheter further comprises a steering assembly, the steering assembly including a pull wire, a pull band, and a control member, the control member being mounted to the distal portion of the handle, the pull band being mounted to the outer tubular member in proximity to the distal end thereof, and the pull wire extending along a length of the outer tubular member from a proximal end of the pull wire to a distal end of the pull wire, the proximal end of the pull wire being coupled to the control member, and the distal end of the pull wire being coupled to the pull band.

8. The system of claim 1, wherein an outer profile of the connector portion is configured to interlock with an inner profile of the cavity of the device holding member.

* * * * *